US008653250B2

(12) United States Patent
Patterson (10) Patent No.: US 8,653,250 B2
(45) Date of Patent: Feb. 18, 2014

(54) HPV E6, E7 MRNA ASSAY AND METHODS OF USE THEREOF (75) Inventor: Bruce K. Patterson, Palo Alto, CA (US)

(73) Assignee: IncellDx, Inc., Menlo Park, CA (US)

(*) Notice: Subject to any disclaimer, the term of this patent is extended or adjusted under 35 U.S.C. 154(b) by 336 days.

(21) Appl. No.: 12/645,202

(22) Filed: Dec. 22, 2009

(65) Prior Publication Data
US 2010/0120021 A1 May 13, 2010

Related U.S. Application Data (63) Continuation of application No. 12/391,634, filed on Feb. 24, 2009, now Pat. No. 7,888,032, which is a continuation of application No. 11/050,384, filed on Feb. 2, 2005, now Pat. No. 7,524,631.

(51) Int. Cl.
C07H 21/04 (2006.01)

(52) U.S. Cl.
USPC .......................................... 536/24.3

(58) Field of Classification Search
None
See application file for complete search history.

(56) References Cited

U.S. PATENT DOCUMENTS

| 6,355,424 B1 | 3/2002 | Lorincz et al. ............. 435/6 |
| 7,326,577 B2 * | 2/2008 | Shults et al. ................ 436/176 |
| 7,524,631 B2 | 4/2009 | Patterson ..................... 435/6 |
| 2005/0164184 A1 * | 7/2005 | Chun ........................... 435/6 |

FOREIGN PATENT DOCUMENTS

| EP | 0373352 | 6/1990 |
| EP | 0662518 | 7/1995 |
| EP | 0774518 | 5/1998 |
| WO | 9426934 | 11/1994 |
| WO | 9929890 | 6/1999 |

OTHER PUBLICATIONS

Sun et al. (Oncogene (1997) 15, 2399-2408).*
Mosiman et al. (Cytometry (Communications in Clinical Cytometry) 30: 151-158) 1997.*
Patterson et al. (Acta Cytologica (Jan.-Feb. 2002) vol. 46, No. 1 Supplement, pp. 206-207. print. Abstract numbered 561.*
Patterson et al. (1998, Cytometry 31: 265-274.*
Braissant et al. (Biochemica, No. 1 (1998), pp. 10-16).*
Ahern et al. Biochemical, Reagent Kits Offer Scientists Good Return on Investment. The Scientist, vol. 9, #15, Jul. 24, 1995, obtained from www.the-scientist.library.upenn.edu on Dec. 22, 1998. five pages.*
Munger. Journal of Virology, Nov. 2004, p. 11451-11460.*
Sotlar et al. Journal of Medical Virology. 2004. 74:107-116.*
Jeon et al. PNAS USA, 1995, 92:1654-1658.*
Patterson et al. Acta Cytologica (Jan.-Feb. 2002) vol. 46, No. 1 Supplement, pp. 206-207. print. Abstract numbered 561.
Patterson, Moisman et al. 1998, Cytometry 31: 265-274.

"Cervical Cancer, What is it?" (2004), printed from www.labstestonline.org on Jun. 9, 2007.
Corkill et al., "Specimen Adequacy of Thinprep Sample Preparations in a Direct-To-Vial Study" ACTA Cytology 41 (1): 39-44 (1997).
Cuschieri et al., "Assessment of Human Papillomavirus mRNA Detection Over Time in Cervical Specimens Collected in Liquid Based Cytology Medium" J. Virological Methods, Amsterdam 124(1-2): 211-215 (2004) Dec. 16, 2004.
Grundhoefer and Patterson, "Determination of Liquid-Based Cervical Cytology Specimen Adequacy Using Cellular Light Scatter and Flow Cytometry" Cytometry 46:340-344 (2001).
Hakama "Screening for Cervical Cancer in Advances in Cancer Screening" (A.B. Miller ed., Kluwer Academic Publishers, Boston; pp. 41-49 (1996).
Kulasingam et al., Evaluation of Human Papillomavirus Testing in Primary Screening for Cervical Abnormalities: JAMA 288(14): 1749-1757 (2002).
McNicol et al., "Expression of Human Papillomavirus Type 16 ES-E7 Open Reading Frame Varies Quantitatively in Biopsy Tissue from Differentiated Grades of Cervical Intraepithelial Neoplasia" J. Clin. Microbiology 33(5): 1169-1173 (1995).
Melinkow et al., "Natural History of Cervical Squamous Intraepithelial Lesions: A Meta-Analysis" J. Obstet. Gynecol. 92(4): 727-735 (1998).
Mosiman, et al., "Reducing Cellular Autofluorescence in Flow Cytometry: an In Situ Method" Cytometry 30:151-156 (1997).
Nanda et al., "Accuracy of the Papanicolaou Test in Screening for and Follow up of Cervical Cytologic Abnormalities: A Systematic Review" Ann. Intern. Med. 132:810-819 (2000).
Patterson et al., "Detection of HIV-RNA-Positive Monocytes in Peripheral Blood of HIV-Positive Patients by Simultaneous Flow Cytometric Analysis of Intracellular HIV RNA and Cellular Immunophenotype" Cytometry 31:265-274 (1998).
Patterson et al., "Monitoring HIV-1 Treatment in Immune-Cell Subsets with Ultrasensitive Fluorescence-In-Situ Hybrdization" Lancet 353:211-212 (1999).
Patterson et al., "Molecular Biomarker-Based Screening for Early Detection of Cervical Cancer" ACTA Cytologica 45(1):36-47 (2001).
Patterson et al., "High Throughput Cervical Cancer Screening Using Intracellular HPV E6, E7 mRNA Quantification by Ultrasensitive Fluorescence In Situ Hybridization and Flow Cytometry" ACTA Cytologica 46(1 Supp): 206-207 (Jan. 2002); and Abstract 14th Int'l Congress of Cytology, Amsterdam Netherlands May 27-31, 2001.

(Continued)

Primary Examiner — Juliet Switzer
(74) Attorney, Agent, or Firm — Bozicevic, Field & Francis LLP; Bret E. Field; Khin K. Chin (57) ABSTRACT Provided is an HPV E6, E7 mRNA assay, referenced herein as the "In Cell HPV Assay," that is capable of sensitive and specific detection of normal cervical cells undergoing malignant transformation as well as abnormal cervical cells with pre-malignant or malignant lesions. The In Cell HPV Assay identifies HPV E6, E7 mRNA via in situ hybridization with oligonucleotides specific for HPV E6, E7 mRNA and quantitates the HPV E6, E7 mRNA via flow cytometry. The In Cell HPV Assay can be carried out in less than three hours directly from liquid-based cervical ("LBC") cytology specimens. The In Cell HPV Assay provides an efficient and highly sensitive alternative to the Pap smear for determining abnormal cervical cytology.

6 Claims, 8 Drawing Sheets (56) References Cited

OTHER PUBLICATIONS

Tarkowski et al., "Improved Detection of Viral RNA Isolated from Liquid-Based Cytology Samples" Molecular Diagnosis 6(2): 125-130 (2001).

Wilbur et al., "Clinical Trials of the CytoRich Specimen-Preparation Device for Cervical Cytology" ACTA Cytologica 41(1): 24-29 (1997).

Woodman et al., "Natural History of Cervical Human Papillomavirus Infection in Young Women: A Logitudinal Cohort Study" Lancet 357:1831-1836 (2001).

Website page on the Norchip Pretect HPV-Proofer printed on Jan. 9, 2005: http://www.norchip.com/html/articles/article-2.html.

Website page on the Norchip Pretect HPV-Proofer printed on Jan. 9, 2005: http://www.norchip.com/html/articles/article-3.html.

Website page on the Norchip Pretect HPV-Proofer printed on Jan. 9, 2005: http://www.norchip.com/html/FAQeng.html.

* cited by examiner

HPV E6, E7 MRNA ASSAY AND METHODS OF USE THEREOF

TECHNICAL FIELD

The invention relates generally to an HPV mRNA assay for the detection of HPV-related disorders such as cervical cancer and cervical lesions. More specifically, the invention relates to an assay that identifies and quantitates HPV E6, E7 mRNA in cervical cells. The HPV E6, E7 mRNA Assay, referenced herein as the "In Cell HPV Assay," is capable of sensitive and specific detection of cancerous and pre-cancerous abnormal cells as well as normal cells undergoing malignant transformation.

BACKGROUND OF THE INVENTION

Cervical cancer affects approximately 13,000 women per year in the United States and more than 400,000 women worldwide. Ninety percent of cervical cancers contain the high risk HPV DNA strains 16 and 18 ("HPV-16" and "HPV-18," respectively). By contrast, low risk HPVs, such as HPV-6 and HPV-11, rarely develop into cancer. The presence of low risk and high risk HPVs are identified through the use of the polymerase chain reaction ("PCR") or the Hybrid Capture® II HPV Test ("HC II HPV Test"; Digene Corp., Gaithersburg, Md.)

The Papanicolaou ("Pap") smear assesses a patient's risk for cervical cancer by testing for the presence of squamous intraepithelial lesions ("SILs") on the cervix. The Pap smear has been the standard of care in the U.S. for over 50 years, resulting in a 74% decline in deaths due to cervical cancer. The Pap smear, however, is not without its shortcomings; in particular, errors in cervical sampling and interpretation contribute to a Pap smear sensitivity of only 58%. Hakama, *Screening for Cervical Cancer*, CANCER TREND RES. 86:41-49 (1996); Nanda et al., *Accuracy of the Papanicolaou Test in Screening for and Follow-up of Cervical Cytologic Abnormalities*, ANN. INTERN. MED. 132:810-819 (2000). In 1996, the Food and Drug Administration approved the ThinPrep® Pap Test (Cytec Corp., Marlborough, Mass.) as an alternative to the conventional Pap smear for the screening of SILs. The ThinPrep Pap Test screens for SILs using liquid based cytology ("LBC") with automated monolayer slide production. The use of LBC has resulted in an increase in adequate specimens and the detection of SILs; however, LBC samples have a sensitivity of only 80%. Corkill et al., *Specimen Adequacy of the ThinPrep Sample Preparations in a Direct-to-Vial Study*, ACTA CYTOL. 41:39-44 (1997); Wilbur et al., *Clinical Trials of the CYTORICH Specimen-Preparation Device for Cervical Cytology*, ACTA CYTOL. 41:24-29 (1997).

While the life cycle of HPV would indicate that women with high risk HPVs will develop either low grade SILs ("LGSILs," i.e., SILs from an early pre-malignant lesion) or high grade SILs ("HGSILs," i.e., SILs from an advanced pre-malignant lesion) and progress to cancer while women with low risk HPVs will not; in reality, only a minority of women infected with high risk HPVs and exhibiting either LGSILs or HGSILs will progress to cancer. The following table shows the rate of regression and progression of women diagnosed via Pap smear or LBC with ASCUS (abnormal squamous cells of undetermined significance), LGSILs, and HGSILs (from Melnikow et al., *Natural History of Cervical Squamous Intraepithelial Lesions: A Meta-Analysis*, J. OBSTET. GYNECOL. 92:727-735 (1998); see also, Woodman et al., *Natural History of Cervical Human Papillomavirus Infection in Young Women: A Longitudinal Cohort Study*, LANCET 357:1831-1836 (2001)):

| CYTOLOGY | REGRESSION TO NORMAL | PROGRESSION TO HIGHER GRADE OVER 24 MONTHS | PROGRESSION TO INVASIVE CANCER OVER 24 MONTHS |
|---|---|---|---|
| ASCUS | 68% | 7% | 0.25% |
| LGSIL | 47% | 21% | 0.15% |
| HGSIL | 35% | 23% | 1.44% |

As the data in the foregoing table demonstrates, the majority of women diagnosed with ASCUS, LGSILs, and HGSILs do not progress to cancer; accordingly, the traditional Pap smear and LBC test, both of which merely identify the presence abnormal SILs are not effective tests to distinguish benign lesions from lesions with malignant potential. Similarly, because the majority of women diagnosed with ASCUS, LGSILs, and HGSILs are usually infected with a high risk HPV, it follows that the identification of infection with a high risk HPV is also not a biologically relevant indicator for cervical cancer detection. There is therefore, a need in the art for a more highly sensitive method by which to screen for cervical cancer.

SUMMARY OF THE INVENTION

The present invention overcomes the need in the aforementioned need in the art by providing assays and method for screening cervical cancer by screening for, detecting, and quantitating intracellular HPV E6, E7 mRNA in cervical cells. TO the best of the inventor's knowledge, no such HPV E6, E7 mRNA assay has been previously published or disclosed.

In a first aspect of the invention, there is provided an assay for determining malignant transformation of cervical cells comprising the steps of: (a) obtaining cervical cells from an individual; (b) preparing the cervical cells as a liquid-based cytology (LBC) specimen; and (c) hybridizing the LBC specimen using oligonucleotides specific for HPV E6, E7 mRNA, wherein expression of HPV E6, E7 mRNA indicates malignant transformation of the cervical cells. Within this aspect of the invention, the HPV E6, E7 mRNA may be quantitated via flow cytometry.

In a second aspect of the invention, there is provided a method of screening a patient for malignant transformation of cervical cells comprising identifying expression of HPV E6, E7 mRNA in the cervical cells. In a preferred embodiment, the HPV E6, E7 mRNA is identified using in situ hybridization with oligonucleotides specific for HPV E6, E7 mRNA and the HPV E6, E7 mRNA is quantitated using flow cytometry.

Generally malignant transformation of the cervical cells is indicated by expression of 2 to 1000 copies of HPV E6, E7 mRNA per cell, with expression of 5 to 750 copies of HPV E6, E7 mRNA per cell preferred, expression of 10 to 500 copies of HPV E6, E7 mRNA per cell more preferred, and expression of 200 or more copies of HPV E6, E7 mRNA per cell most preferred.

The cervical cells that may be used in both the assay and the method described above are selected from the group consisting of normal cells, abnormal squamous cells of undetermined significance (ASCUS), cells with low grade squamous intraepithelial lesions (LGSILs), and cells with high grade intraepithelial lesions (HGSILs).

In a third aspect of the invention, there is provided a method of screening a patient with abnormal cervical cells for premalignant cervical cells, comprising quantitating the expression of HPV E6, E7 mRNA in the cervical cells, wherein cells expressing 200 or more copies of HPV E6, E7 mRNA per cell indicate cells with malignant potential and cells expressing less than 200 copies of HPV E6, E7 mRNA indicate benign cells. The abnormal cervical cells are selected from the group consisting of abnormal squamous cells of undetermined significance (ASCUS), cells with low grade squamous intraepithelial lesions (LGSILs), and cells with high grade intraepithelial lesions (HGSILs). In a preferred embodiment, the HPV E6, E7 mRNA is identified using in situ hybridization with oligonucleotides specific for HPV E6, E7 mRNA and the HPV E6, E7 mRNA is quantitated using flow cytometry.

In a fourth aspect of the invention, there is provided an assay for identifying malignantly transformed cervical cell types comprising the steps of (a) obtaining cervical cells from an individual; (b) preparing the cervical cells as a liquid-based cytology (LBC) specimen; (c) staining the cervical cells with a combination of CD16 and CAM 5.2; and (d) hybridizing the LBC specimen using oligonucleotides specific for HPV E6, E7 mRNA, wherein neutrophils are identified by CD16$^+$ staining, columnar endocervical cells are identified by CD16$^-$, CAM 5.2$^+$ staining, and squamous ectocervical cells are identified by CD16$^-$, CAM 5.2$^-$ staining, and expression of HPV E6, E7 mRNA indicates malignant transformation of the cervical cells. Within this aspect of the invention, the expression of HPV E6, E7 mRNA per cell may be quantitated via flow cytometry, with malignant transformation of the cervical cells indicated by expression of 2 to 1000 copies of HPV E6, E7 mRNA per cell, with expression of 5 to 750 copies of HPV E6, E7 mRNA per cell preferred, expression of 10 to 500 copies of HPV E6, E7 mRNA per cell more preferred, and expression of 200 or more copies of HPV E6, E7 mRNA per cell most preferred. Malignantly transformed columnar endocervical cells indicate a pre-adenocarcinoma or adenocarcinoma cervical condition and malignantly transformed squamous ectocervical cells indicate pre-squamous cell carcinoma or squamous cell carcinoma cervical condition.

Additional aspects, advantages and features of the invention will be set forth, in part, in the description that follows, and, in part, will become apparent to those skilled in the art upon examination of the following, or may be learned by practice of the invention.

BRIEF DESCRIPTION OF THE DRAWINGS

FIGS. 3A-3E collectively show the detection and morphology of abnormal and normal cells stained on slides (scale bar 20 μm).

FIGS. 4A-4I show flow cytometry histograms of normal and abnormal cervical cells gated by light scatter, stained with a combination of CD16$^-$ and CAM 5.2$^-$ to identify ectocervical cells, and analyzed for HPV E6, E7 mRNA expression using the In Cell HPV Assay of the present invention.

DETAILED DESCRIPTION OF THE INVENTION

Definitions and Nomenclature

Before describing detailed embodiments of the invention, it will be useful to set forth definitions that are used in describing the invention. The following definitions are used in describing the invention. The terminology used in the definitions is for the purpose of describing the particular embodiments of the invention and is not intended to be limiting.

As used in this specification and the appended claims, the singular forms "a," "an," and "the" include plural referents unless the context clearly dictates otherwise.

The term "In Cell HPV Assay" refers to the simultaneous immunofluorescence and ultrasensitive fluorescence in situ hybridization assay described in Examples 1 and 2. The In Cell HPV Assay is capable of identifying cancerous and precancerous SILs by detecting the presence of very low copies of HPV E6, E7 mRNA in the SILs. Where appropriate, the HPV E6, E7 mRNA detected by the In Cell HPV Assay may be quantitated using flow cytometry; thus, as used herein, the term "In Cell HPV Assay" is used generally to refer to the identification and where appropriate, the quantitation of the HPV E6, E7 mRNA.

The term "Bethesda System" refers to the currently used classification system for Pap smear and ThinPrep Pap test analysis. The Bethesda System is described at www.cytopathology.org/NIH and includes the classifications WNL, ASCUS, LGSIL, and HGSIL already referenced herein as well as the term "squamous cell carcinoma" for malignantly transformed cervical cells. The Bethesda System classifications are also referenced herein as "cytologies."

As used herein, the term "cervical cells" refers generally to the squamous epithelial cells that line the surface of the cervix. The term is used generally to include normal cervical cells as well the abnormal cervical cells, i.e., ASCUS, LGSILs, HGSILs, and squamous cell carcinomas.

The term "squamous intraepithelial lesions" or "SILs" refers to lesions that form on the cervical squamous cells and includes both the low grade (LGSILs) and the high grade (HGSIL) lesions.

The term "adenocarcinoma" and "squamous cell carcinoma" are used conventionally to refer to malignant epithelial cell tumors of the glands (adenocarcinoma) and malignant tumors of the squamous epithelium (squamous cell carcinoma). The terms "pre-adenocarcinoma" and "pre-squamous cell carcinoma" refer to lesions that have not yet been malignantly transformed. As used herein, the terms adenocarcinomas and pre-adenocarcinomas refer to tumors and lesions of the glandular epithelium of the cervix and the terms squamous cell carcinomas and pre-squamous cell carcinomas refer to tumors and lesions of the squamous epithelial cells of the cervix.

The term "nucleic acid analyte" refers generally to all nucleic acids, such as all DNAs and RNAs, and segments thereof. Within the context of the present invention, the term includes DNA, RNA, and mRNA.

As used herein, the term "target amplification" refers to enzyme-mediated procedures that are capable of producing billions, of copies of nucleic acid target. Examples of enzyme-mediated target amplification procedures known in the art include PCR, nucleic acid-sequence-based amplification ("NASBA"), transcription-mediated amplification ("TMA"), strand displacement amplification ("SDA"), and ligase chain reaction ("LCR").

The most widely used target amplification procedure is. PCR, first described for the amplification of DNA by Mullins et al. in U.S. Pat. No. 4,683,195 and Mullis in U.S. Pat. No. 4,683,202. The PCR procedure is well known to those of ordinary skill in the art. Where the starting material for the PCR reaction is RNA, complementary DNA ("cDNA") is made from RNA via reverse transcription. A PCR used to amplify RNA products is referred to as reverse transcriptase PCR or "RT-PCR."

As used herein, the term "type specific PCR" refers to the use of PCR to identify high risk and low risk HPV DNA.

Real-time PCR and Real-time RT-PCR refers to the detection of PCR products via a fluorescent signal generated by the coupling of a fluorogenic dye molecule and a quencher moiety to the same or different oligonucleotide substrates. Examples of commonly used probes used in real-time PCR and real-time RT-PCR include the following probes: Taqman® probes, Molecular Beacons probes, Scorpions® probes, and SYBR® Green probes. Briefly, Taqman probes, Molecular Beacons, and Scorpion probes each have a fluorescent reporter dye (also called a "fluor") attached to the 5' end of the probes and a quencher moiety coupled to the 3' end of the probes. In the unhybridized state, the proximity of the fluor and the quench molecules prevents the detection of fluorescent signal from the probe; during PCR, when the polymerase replicates a template on which a probe is bound, the 5'-nuclease activity of the polymerase cleaves the probe thus, increasing fluorescence with each replication cycle. SYBR Green probes binds double-stranded DNA and upon excitation emit light; thus as PCR product accumulates, fluorescence increases.

Within the context of the present invention, real-time RT-PCR is used to identify oncogenic mRNA in abnormal cervical samples, such as for example, the E6 mRNA found in HPV-16 and HPV-18. Real-time RT-PCR is used in Examples 6 and 7 with a Taqman probe. Taqman probes are designed to hybridize to an internal region of a PCR product. In the unhybridized state, the proximity of the fluor and the quench molecules prevents the detection of fluorescent signal from the probe; during PCR, when the polymerase replicates a template on which a Taqman probe is bound, the 5'-nuclease activity of the polymerase cleaves the probe thus, increasing fluorescence with each replication cycle.

The term "signal amplification" refers to techniques that are capable of detecting and quantitating the amount of nucleic acid analyte in a sample by amplifying the signal of a target in direct proportion to the amount of target. Because the amount of target is not altered, signal amplification procedures are useful for quantitating the amount of nucleic acid analyte in as sample. Examples of signal amplification procedures known in the art include branched DNA ("bDNA") signal amplification (Bayer Healthcare LLC, Tarrytown, N.Y.), Hybrid Capture ("HC"; Digene Corp., Gaithersburg, Md.), and Tyramide Signal Amplification ("TSA," Perkin Elmer, Inc., Wellesley, Mass.).

Within the context of the present invention, the HC II HPV Test is a signal amplification assay used to detect the presence of HPV DNA in clinical samples. The HC II HPV Test includes the following steps: clinical specimens are combined with a base solution that disrupts the virus and releases target DNA; target DNA combines with specific RNA probes creating RNA:DNA hybrids; multiple RNA hybrids are captured onto a solid phase coated with universal capture antibodies specific for RNA:DNA hybrids; captured RNA:DNA hybrids are detected with multiple antibodies conjugated to alkaline phosphatase ("AP"; amplification may reach 3000 fold); and the bounds alkaline phosphatase is detected with a chemiluminscent dioxetane substrate. Upon cleavage by AP, the substrate produces light that may be measured on a luminometer in relative light units ("RLUs"). The HC II HPV Test is capable of detecting 13 high-risk HPV types: HPV-16, HPV-18, HPV-31, HPV-33, HPV-35, HPV-39, HPV-45, HPV-51, HPV-52, HPV-56, HPV-58, HPV-59, and HPV-68.

Identiyfing and Quantitating HPV E6, E7 mRNA

The present invention provides an HPV E6, E7 mRNA assay (the In Cell HPV Assay) that identifies pre-cancerous and cancerous cervical cells by detecting the presence of HPV E6, E7 mRNA in the cells. Because HPV E6, E7 mRNA is a highly sensitive biomarker for the detection of malignant transformation of cervical cells, the In Cell HPV Assay described herein is capable of detecting malignant transformation of cervical cells that exhibit normal cytology in addition to cells exhibiting abnormal cytology, e.g., ASCUS, LGSILs, and HGSILs (Examples 6 and 7).

The In Cell HPV Assay consists of an in situ hybridization assay performed with HPV E6, E7 mRNA oligonucleotide probes, and where appropriate, flow cytometry to quantitate the HPV E6, E7 mRNA. Examples 1 and 2 describe two different in situ hybridization methodologies to carry out the In Cell HPV Assay and Example 3 describes the use of flow cytometry to quantitate the HPV E6, E7 mRNA.

Based upon the foregoing principles, in a first embodiment of the present invention, there is provided an assay for determining cytology of cervical cells comprising the steps of: (a) obtaining cervical cells from an individual; (b) preparing the cervical cells as an LBC specimen; and (c) hybridizing the LBC specimen using oligonucleotides specific for HPV E6, E7 mRNA, wherein expression of HPV E6, E7 mRNA indicates malignant transformation of the cervical cells. Within this first embodiment of the present invention, the HPV E6, E7 mRNA may be quantitated via flow cytometry.

In a second embodiment of the present invention, there is provided a method of screening a patient for malignant transformation of cervical cells comprising identifying expression of HPV E6, E7 mRNA in the cervical cells. Within this second embodiment, the HPV E6, E7 mRNA is identified using in situ hybridization and the HPV E6, E7 mRNA is quantitated using flow cytometry.

In both the assay and method of the first and second embodiments of the present invention, the cervical cells are selected from the group consisting of normal cells, abnormal squamous cells of undetermined significance (ASCUS), cells with low grade squamous intraepithelial lesions (LGSILs), and cells with high grade intraepithelial lesions (HGSILs). As mentioned above, a significant advantage of the In Cell HPV Assay over the other available methods of detecting cervical cell cytology is that the In Cell HPV Assay, through the detection of HPV E6, E7 mRNA expression, is capable of identifying early malignant transformation in otherwise normal appearing cells. None of the presently available methods of cervical cell screening are capable of such sensitivity and specificity. The ability of the In Cell HPV Assay to detect HPV E6, E7 mRNA in cells with normal cytology is described in Examples 6 and 7. In Example 6, 3 of 41 high risk women with normal cervical cytology tested positive for HPV E6, E7 mRNA using the In Cell HPV Assay and in Example 7, 10 of 109 low risk women tested positive for HPV E6, E7 mRNA; thus, indicating malignant transformation in the "normal" cells of these women.

As noted above, the diagnostic results of the In Cell HPV Assay were confirmed in Examples 6 and 7 using real-time RT-PCR and in Example 7 using both real-time RT-PCR and the HC II HPV Test. As previously noted, and as reiterated in Example 7, the In Cell HPV Assay of the present invention is superior over the HC II HPV Test for the detection of cervical cancer because the In Cell HPV Assay is capable of detecting malignantly transformed cells at a very early stage, while the HC II HPV Test only detects high risk HPV DNA, i.e., HPV-16 and HPV-18, both of which are not indicators of malignant transformation of cells. The In Cell HPV Assay is also superior over the use of real-time RT-PCR for the detection of cervical cancer because unlike real time PCR, which is a target amplification procedure that can only identify amplification of a population of cells, the In Cell HPV Assay is a highly specific procedure that is capable of identifying amplification of an individual cell. In other words, comparing the amplification of one million copies of HPV E6, E7 mRNA derived by real time RT-PCR versus one million copies of HPV E6, E7 mRNA derived by the In Cell HPV Assay of the present invention, the real-time RT-PCR will only be able to discern that one-million copies of the gene have been produced; by contrast, the In Cell HPV Assay is capable of discerning exactly how many cells have produced the one million copies. Thus, under real-time RT-PCR, the ordinary practitioner will be unable to identify if one million individual cells produced the one million copies as occurs in a normal individual or if one thousand cells produced one thousand cells each as occurs in cancer. The In Cell HPV Assay of the present invention overcomes this deficiency in real-time RT-PCR by identifying, via flow cytometric quantitation, the precise number of copies of HPV E6, E7 mRNA that are produced per cell. In this way, in Examples 6 and 7, the real-time RT-PCR was used only to verify the presence of HPV E6, E7 mRNA.

In both the first and second embodiments of the present invention, the malignant transformation of the cervical cells is indicated by expression of 2 to 1000 copies of HPV E6, E7 mRNA per cell, with expression of 5 to 750 copies of HPV E6, E7 mRNA per cell preferred, expression of 10 to 500 copies of HPV E6, E7 mRNA per cell more preferred, and expression of 200 or more copies of HPV E6, E7 mRNA per cell per cell most preferred. While the theoretical sensitivity of the flow cytometric analysis in Example 3 was found to be 10 to 20 copies of HPV E6, E7 mRNA, further calibration of the flow cytometric assay should theoretically reduce the sensitivity of the flow cytometric analysis to as low as one to two copies of HPV E6, E7 mRNA and as high as 1000 copies of HPV E6, E7 mRNA per cell.

In a third embodiment of the present invention, there is provided a method of screening a patient with abnormal cervical cells for pre-malignant cervical cells, comprising quantitating the expression of HPV E6, E7 mRNA in the cervical cells, wherein cells expressing 200 or more copies of HPV E6, E7 mRNA per cell indicate cells with malignant potential and cells expressing less than 200 copies of HPV E6, E7 mRNA indicate benign cells. The abnormal cells that may be tested in this third embodiment may be selected from the group consisting of abnormal squamous cells of undetermined significance (ASCUS), cells with low grade squamous intraepithelial lesions (LGSILs), and cells with high grade intraepithelial lesions (HGSILs). Similar to the previously discussed embodiments, the HPV E6, E7 mRNA is identified via in situ hybridization and quantitated via flow cytometry.

Where desired, the specific morphology of the cervical cells may be determined by the procedure set forth in Example 5 and depicted in FIG. 3. Specifically, by staining cervical cells with a combination of CD16 (a neutrophil marker) and CAM 5.2 (an antibody expressed in endocervical cells but not ectocervical cells), it is possible to identify the cytology of the cells expressing the HPV E6, E7 mRNA. In a similar vein, the antibody staining formula of Example 5 may also be used to study a specific class of cells, such as the expression levels of HPV E6, E7 mRNA in squamous ectocervical cells from a specific high risk or low risk cohort. (Example 6).

Based upon the principles exemplified in Examples 5 and 6, the fourth embodiment of the present invention provides an assay that simultaneously phenotypes malignantly transformed cells. This assay, for identifying malignantly transformed cervical cell types includes the following steps: (a) obtaining cervical cells from an individual; (b) preparing the cervical cells as a liquid-based cytology (LBC) specimen; (c) staining the cervical cells with a combination of CD16 and CAM 5.2; and (d) hybridizing the LBC specimen using oligonucleotides specific for HPV E6, E7 mRNA, wherein neutrophils are identified by $CD16^+$ staining, columnar endocervical cells are identified by $CD16^-$, $CAM\ 5.2^+$ staining, and squamous ectocervical cells are identified by $CD16^-$, $CAM5.2^-$ staining, and expression of HPV E6, E7 mRNA indicates malignant transformation of the cervical cells. Malignantly transformed columnar endocervical cells indicate a pre-adenocarcinoma or adenocarcinoma cervical condition and malignantly transformed squamous ectocervical cells indicate pre-squamous cell carcinoma or squamous cell carcinoma cervical condition. Like the first and second embodiments described above, expression of HPV E6, E7 mRNA per cell may be quantitated via flow cytometry, with malignant transformation of the cervical cells indicated by expression of 2 to 1000 copies of HPV E6, E7 mRNA per cell, with expression of 5 to 750 copies of HPV E6, E7 mRNA per cell preferred, expression of 10 to 500 copies of HPV E6, E7 mRNA per cell more preferred, and expression of 200 or more copies of HPV E6, E7 mRNA per cell most preferred.

Utility:

The In Cell HPV Assay described herein is useful as a highly sensitive and specific screening method for the detection of pre-cancerous and cancerous cervical cells, which may be performed in less than three hours. The In Cell HPV Assay is premised on the identification and quantitation of HPV E6, E7 mRNA, where the presence of elevated levels of HPV E6, E7 mRNA in cervical cells indicates the malignant transformation of the cells.

The In Cell HPV Assay is superior over presently available methods for cervical cell screening in that it can detect malignant transformation in cells exhibiting a normal cytology. Because of its remarkable sensitivity and specificity, the In Cell HPV Assay has utility as an alternative and superior primary cervical cell screening method over the traditional Pap smear or the ThinPrep Pap test, both of which merely identify abnormal cervical cells (i.e., ASCUS, LGSILs, and HGSILs), and PCR and the HC II HPV Test, both of which merely identify high risk from low risk HPV. As previously explained, neither cervical cytology nor the identification of low risk or high risk HPVs are reliable markers for determining cervical cell malignancy. For those situations where PCR or the HC II HPV Test is used, the In Cell HPV Assay finds utility as a secondary marker for patients that are HPV DNA positive. In other words, upon primary screening of HPV DNA via PCR or HC II HPV, the In Cell HPV Assay may be used to determine if the SILs exhibiting high risk HPV DNA have been malignantly transformed.

In addition to the foregoing, the In Cell HPV Assay also finds utility as a highly desirable alternative cervical cell screening method in that it is capable of being performed in less than three hours with established experimental protocols. The foregoing demonstrates that the In Cell HPV Assay is not only more accurate than any presently used methods to detect malignant transformation of cervical cells, but it is also more time and cost effective.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, publications, and other published documents mentioned or referred to, both supra and infra, are incorporated by reference in their entireties.

The following examples are put forth so as to provide those of ordinary skill in the art with a complete disclosure and description of how to make and use the compositions of the invention. Efforts have been made to ensure accuracy with respect to numbers (e.g., amounts, temperature, etc.) but some experimental error and deviations should, of course, be allowed for. Unless indicated otherwise, parts are parts by weight, temperature is degrees centigrade and pressure is at or near atmospheric. All components were obtained commercially unless otherwise indicated.

EXPERIMENTAL

Unless otherwise indicated, all formulations described herein were performed with commercially available products. The following protocols were used in the Examples.

Subjects: Women undergoing routine cervical cytology at multiple sites were enrolled in a study following informed consent. Cervical cytology specimens were collected using a cytobrush and preserved using SurePath™ (Tripath Ithaging, Burlington, N.C.) liquid-based cytology fixative. The smears were classified using The Bethesda System.

Cell Lines: HeLa cells were obtained from the American Type Culture Collection (Manassas, Va.) and grown according to instructions. Normal human ectocervical cells (Clonetics, Inc., now Cambrex, Inc., East Rutherford, N.J.) were grown in media supplied by the company.

Real-Time RT-PCR and HC II HPV Test: For target amplification of oncogenic mRNA, real-time RT-PCR was performed using Taqman® probes (Applied Biosystems, Foster City, Calif.). For signal amplification, the HC II HPV Test was performed according to the manufacture's instructions using a high risk panel of probes.

Cytometry: Flow cytometry was performed using three-color analysis on a FACScan (BDIS, San Jose, Calif.) cytometer. Analysis was restricted to ectocervical cells defined by light scatter characteristics and the lack of expression of the low molecular weight cytokeratin CAM 5.2. Polymorphonuclear neutrophils ("PMN") were excluded from the analysis by gating on cells positive for the PMN marker CD16.

Image Analysis: Image analysis was performed using an Olympus® laser confocal microscope. Cells were included in the analysis if they exhibited green fluorescence (fluorescein, HPV E6, E7 mRNA+) and blue fluorescence (DAPI, all cells) but lacked red fluorescence (PMNs, endocervical cells).

Statistical Analysis: Statistical analyses were performed using either a t-test or a Mann-Whitney Rank Sum test. P values<0.05 were considered statistically significant.

Example 1

Simultaneous Immunofluorescence and Ultrasensitive Fluorescence In Situ Hybridization to Detect HPV E6, E7 ("In Cell HPV Assay")

A 1 mL aliquot was removed from the liquid-based cervical cytology specimen isolated from the subjects. The cells were pelleted by centrifugation at 400×g and washed once in phosphate buffered saline ("PBS"), pH 7.4. Cells were resuspended in 100 µl of PBS, pH 7.4 and stained with a 1:10 dilution of phycoerythrin ("PE")-conjugated anti-CAM 5.2 and PE/cy5-conjugated anti-CD16 (BDPharmingen, San Diego, Calif.). The cells were then incubated at 4° C. for 20 minutes in the dark. Following incubation, the cells were fixed, permeabilized, washed once in PBS, pH 7.4, pelleted by centrifugation at 400×g, washed again in 2×SSC, and pelleted by centrifugation. The cells were then resuspended in a hybridization mix consisting of 5×SSC, 30% formamide, and 100 µg/mL sheared salmon sperm DNA ("ssDNA") and a cocktail of 5'- and 3'-fluorescein labeled HPV E6, E7 mRNA oligonucleotide probes, which may be obtained from Invirion, Inc., Frankfort, Mich., under the name "HPV Onco-Tect," or may be prepared by techniques for the preparation of oligonucleotides known in the art. See e.g., Caruthers et al., *Chemical Synthesis of Deoxyoligonucleotides by the Phosphoramidite Method*, METHODS ENZYMOL 154:287-313 (1987). Hybridization was performed at 37° C. for 30 minutes and was followed by a 5 minute wash in 2×SSC, 0.1% Triton X-100, and a 15 minute wash in 0.1% SSC, 0.1% Triton X-100.

Cells prepared as such were resuspended in PBS, pH 7.4 with 2% fetal calf serum for flow cytometric analysis.

Example 2

The Slide-Based In Cell HPV Assay

100 µL of cells (1×10$^6$ cells/mL) were transferred from the liquid based cervical cytology specimen isolated from the subjects and put into a cytocentrifuge or liquid-based slide system. The slides were centrifuged at 800×g for 2 minutes at room temperature. Following a wash in 1×PBS, pH 7.4, the slides were incubated in 1× PermiFlow (Invirion, Inc., Frankfort, Mich.) fixation/permeabilization reagent in a Coplin jar at room temperature for 1 hour. The slides were then washed once in PBS and once in 2×SSC. The cells were hybridized to a cocktail of the HPV OncoTect probes a hybridization oven at 37° C. for 30-120 minutes. The slides were then washed for 5 minutes in a Coplin jar containing 50 mL pre-heated 2×SSC, 0.1% Triton X-100 and incubated for 15 minutes in a Coplin jar containing 50 mL pre-heated 0.1×SSC, 0.1% Triton X-100. Following a brief rinse in PBS, pH 7.4, the slides were coverslipped using Fluorsave mounting medium (Cal-BioChem, San Diego, Calif.).

Example 3

Validation of the In Cell HPV Assay

Figure 1:
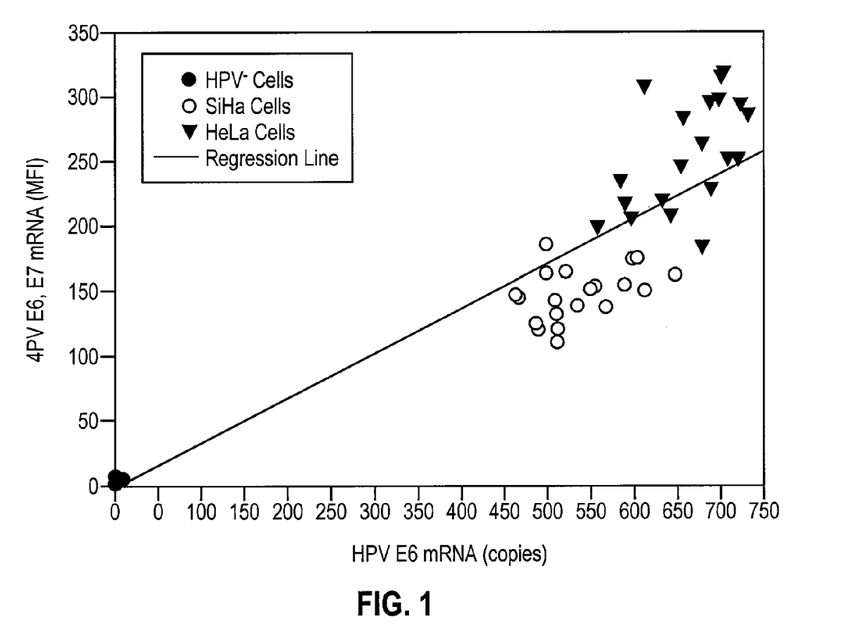
FIG. 1 is a graph showing the relationship between the mean fluorescence intensity ("MFI") of HPV E6, E7 mRNA quantitated by the In Cell HPV Assay using flow cytometry for quantification versus copies of HPV E6 mRNA quantitated by real-time reverse transcriptase PCR ("real-time RT-PCR") in HPV$^-$ normal ectocervical cells and HPV$^+$ SiHa and HeLa cells.

To validate the effectiveness of the In Cell HPV Assay, commercially available normal ectocervical cells, i.e., HPV$^-$ ectocervical cells, and HPV$^+$ SiHa and HeLa cells were grown in culture and split into 20 samples and analyzed for HPV E6, E7 mRNA by the In Cell HPV Assay with flow cytometry and for HPV E6 mRNA by real-time RT-PCR with a detection limit of 10 copies per cell. FIG. 1 shows the relationship between the MFI of HPV E6, E7 mRNA and copies of HPV E6 mRNA in each of the cell populations. Linear regression analysis of the results of FIG. 1 resulted in a correlation of 0.88 with a p value of 0.001. Based upon the results of this experiment, the theoretical sensitivity of the In Cell HPV Assay was calculated to be 10 to 20 copies of HPV E6, E7 mRNA per cell. In all subsequent patient sample analyses, cells were considered positive for HPV E6, E7 mRNA if they exhibited an MFI greater than 200 copies per cell, 200 representing a copy number of HPV that may not be readily cleared from an average patient.

Figure 2:
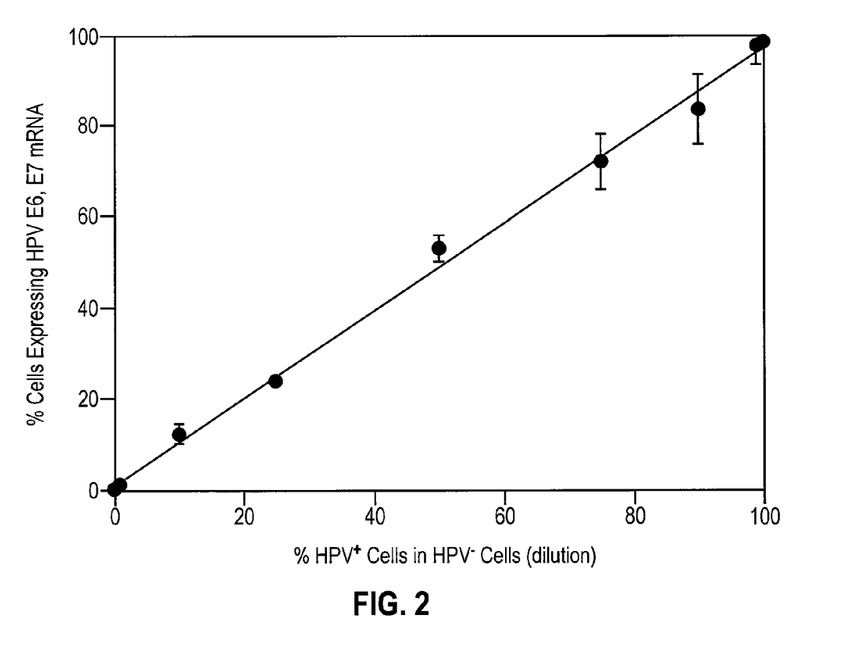
FIG. 2 is a graph showing the linear relationship between serial dilutions of a mixed population of HPV$^+$ HeLa cells in HPV$^-$ normal ectocervical cells versus the percentage of cells in the mixed population expressing HPV E6, E7 mRNA quantitated by the In Cell HPV Assay using flow cytometry.
Figure 3A:
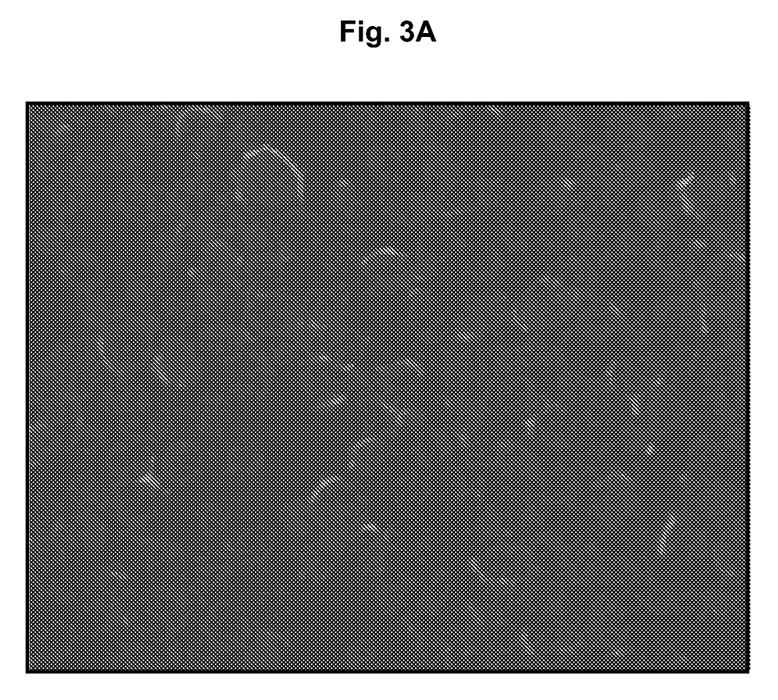
FIG. 3A shows the morphology of abnormal cells expressing HPV E6, E7 mRNA
Figure 3B:
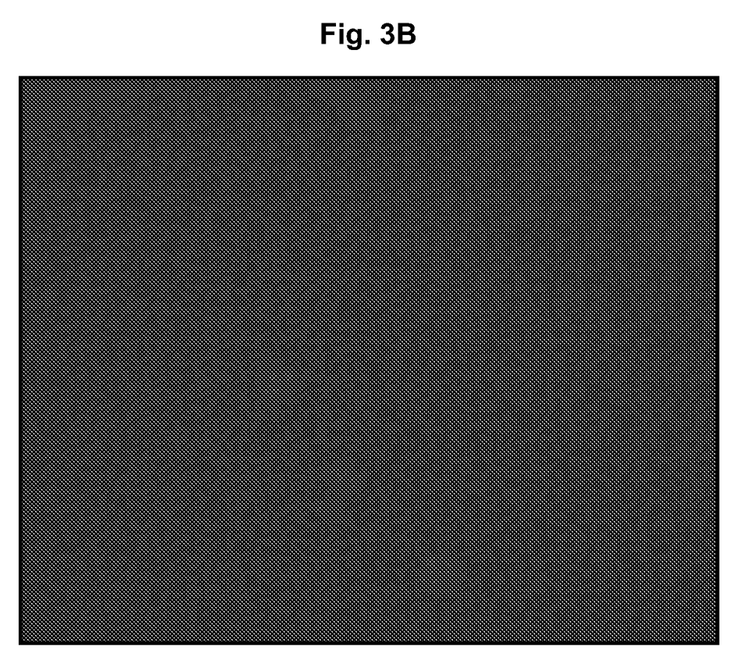
FIG. 3B shows the morphology of normal squamous epithelial cells.
Figure 3C:
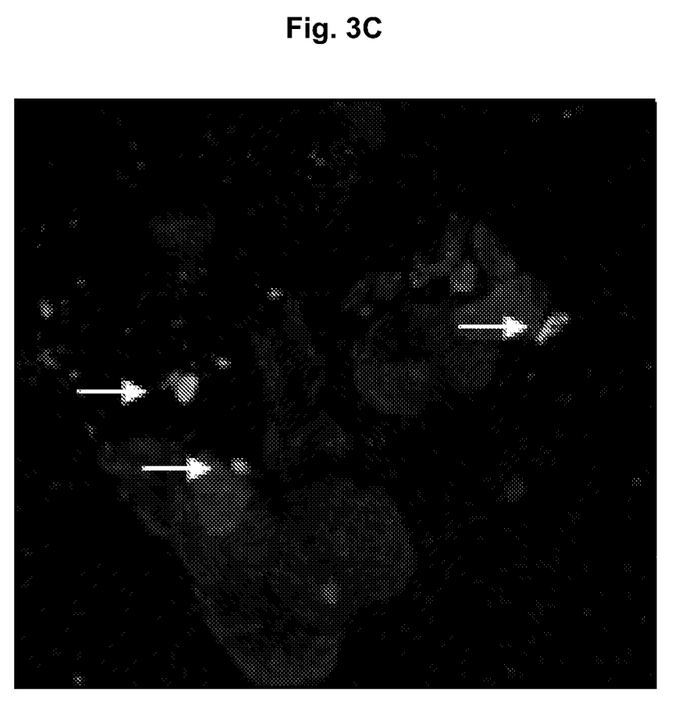
FIGS. 3C-3E show that the abnormal cells have a characteristically high nuclear to cytoplasmic ratio (arrows) whereas the normal cells exhibit a low nuclear to cytoplasmic ratio (arrowheads).
Figure 3D:
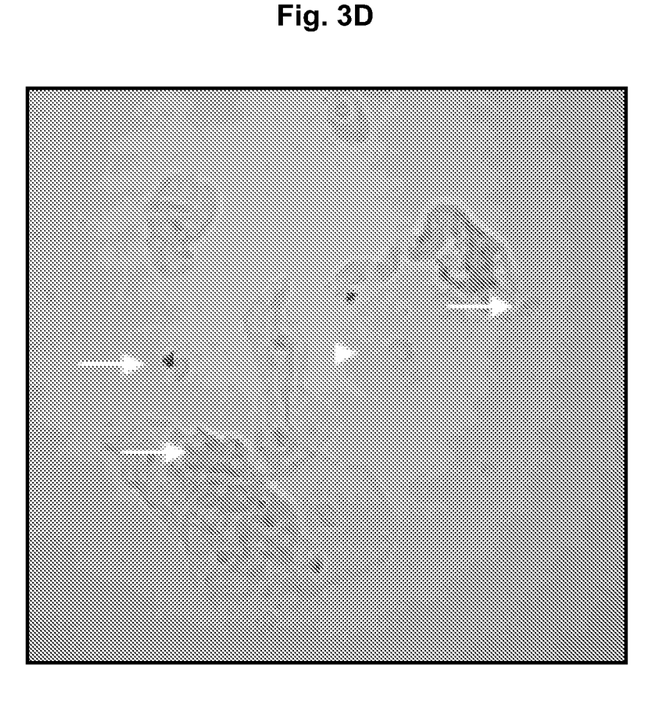
Figure 3E:
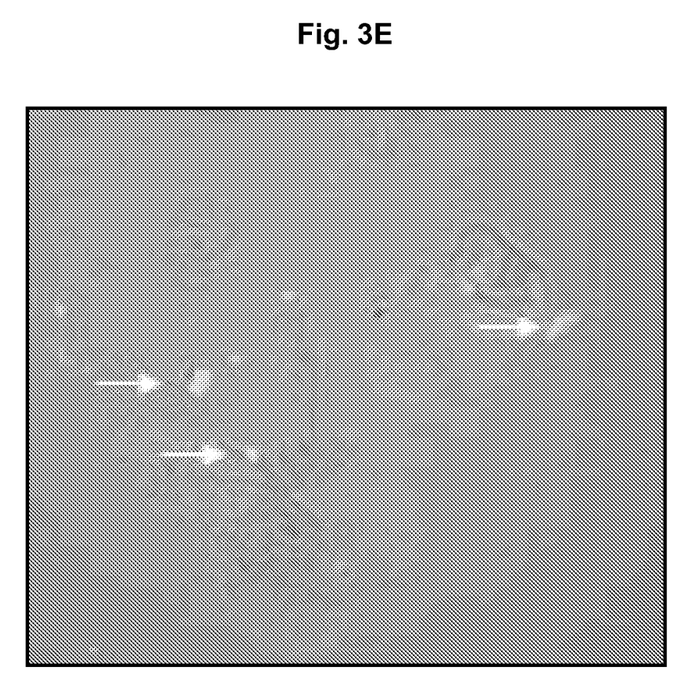

To validate the sensitivity and specificity of the In Cell HPV Assay at the single cell level, the In Cell HPV Assay with flow cytometry were used to quantitate HPV E6, E7 mRNA in a mixed cell population of HeLa cells (HPV$^+$) in normal ectocervical cells (HPV$^-$). As shown in FIG. 2, when the serial dilutions of the mixed cells (% HPV$^+$ cells) were plotted against the percentage of cells expressing HPV E6, E7 mRNA in the mixed cell population as determined by the In Cell HPV Assay; the result was a linear range between 03% and 100% for HPV E6, E7 mRNA positive cells. The signal to noise ratio in this experiment was calculated at 1.5 to 2.0 logs.

Example 4

Morphological Assessment of HPV E6, E7 mRNA Message in Abnormal Cells

To confirm the specificity of the In Cell HPV Assay to detect abnormal cells, HPV$^+$ HeLa cells and HPV$^-$ normal ectocervical cells were hybridized with the HPV E6, E7 mRNA OncoText probes and the morphology of cells expressing detectable levels of HPV E6, E7 mRNA message were examined (FIG. 3). The In Cell HPV Assay produced a characteristic cytoplasmic staining pattern in HeLa cells. By contrast, the HPV$^-$ cell line did not stain (the C33A line was used) (Boxes A and B, respectively). Using the same probe cocktail used in flow cytometry, atypical cells were detected by their characteristic high nuclear to cytoplasmic ratio in a field of many normal squamous cells (Boxes C to E). An overlay image of the Nomarski phase contrast image with a 488 nM fluorescence confocal image confirmed the localization of the hybridization signal over the abnormal cells.

Example 5

Figure 4A:
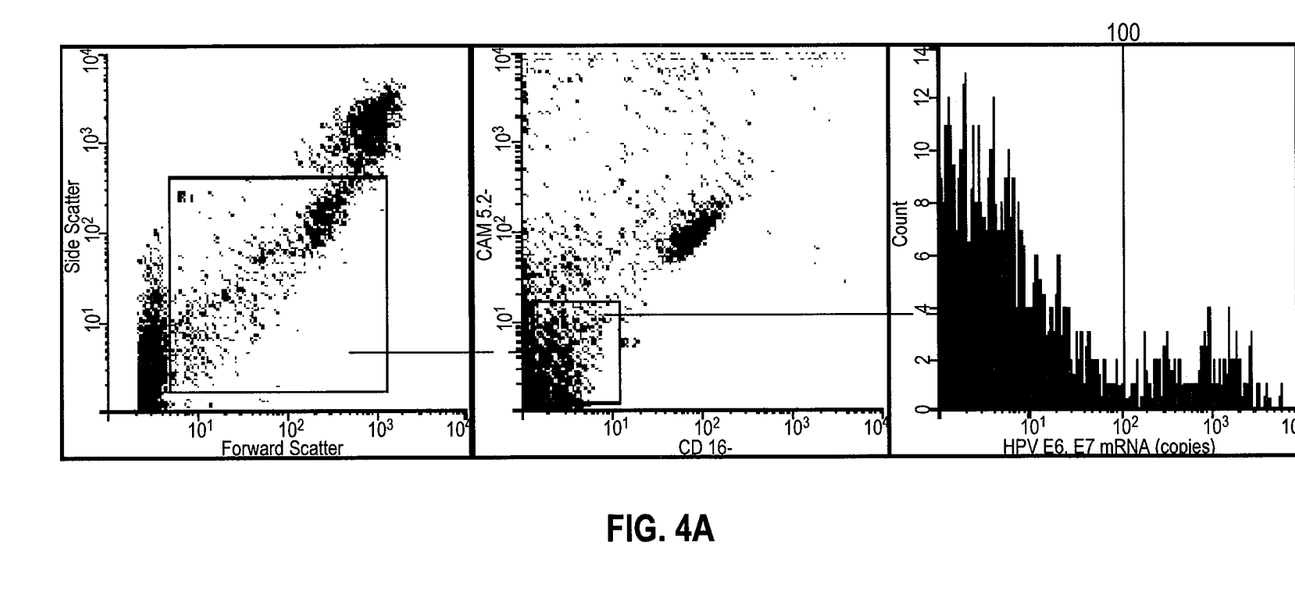
FIG. 4A shows the analysis of cervical cells by forward and side scatter (first box) with a sample (first inner box) selected for staining for ectocervical cells (second box) and with a selected sample (second inner box) of ectocervical cells analyzed for HPV E6, E7 mRNA using the In Cell HPV Assay with 100 copies per cell used as the cut-off point for determining the percentage of cells in a sample expressing HPV E6, E7 mRNA.
Figure 4B:
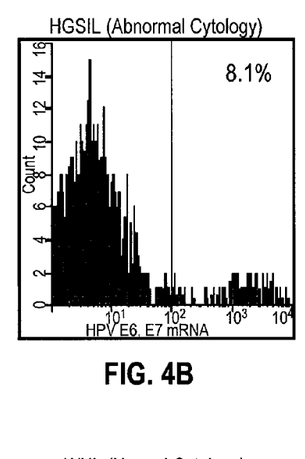
FIGS. 4B-4E show the assay applied to four women with abnormal cytology (HGSIL) and FIGS. 4F-4I show the assay applied to four women with normal cytology (WNL). The percentage of cells expressing more than 100 copies of HPV E6, E7 mRNA per cell in each sample is indicated in the upper right hand corner of the boxes.
Figure 4C:
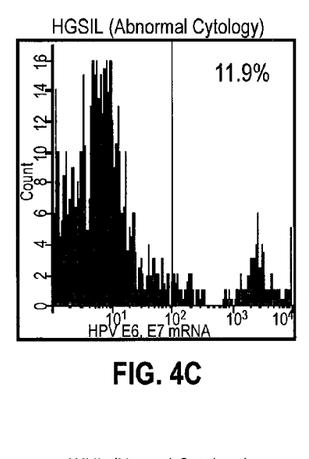
Figure 4D:
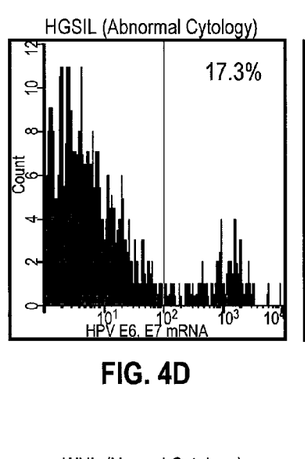
Figure 4E:
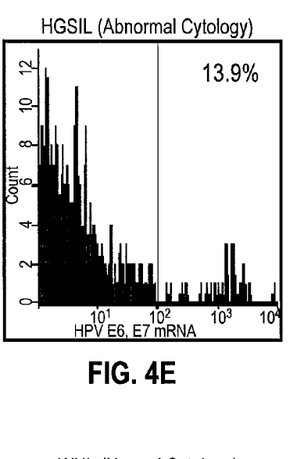
Figure 4F:
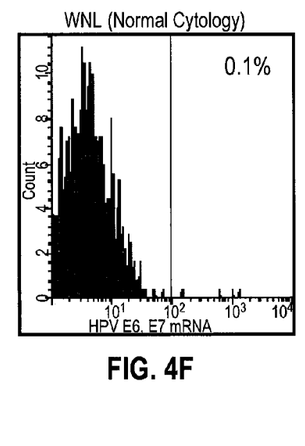
Figure 4G:
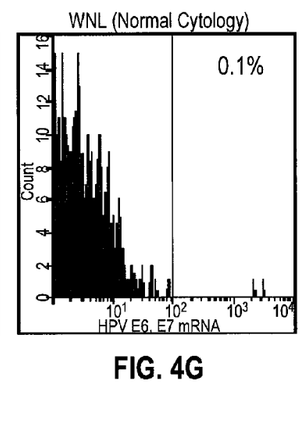
Figure 4H:
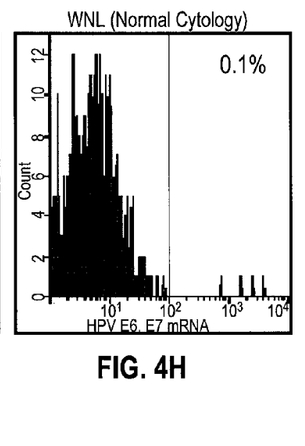
Figure 4I:
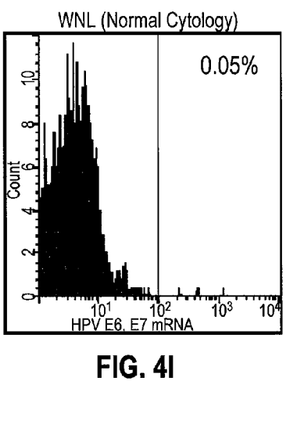

Cytometric Enrichment for HPV E6, E7 Expressing Cells in a Heterogeneous Cervical Cytology Sample Since cervical cytology specimens contain numerous cell types including, but not limited to, squamous ectocervical cells, columnar endocervical cells, PMNs (polymorphonuclear leukocytes), and lymphocytes, an antibody cocktail was developed to be used in conjunction with the In Cell HPV Assay in order to distinguish the cell types of interest in an LBC specimen. To distinguish between ectocervical cells, endocervical cells, and PMNs in LBC preparations of study subjects, the cervical cell specimens were stained with a combination of CD16, a neutrophil marker, and CAM 5.2, an antibody that detects a 70 kDa molecular weight cytokeratin that is expressed in endocervical cells but not ectocervical cells. Cells staining for a particular marker were backgated to identify their presence within forward and orthogonal (90° side scatter) light scatter gates to distinguish between ectocervical cells, endocervical cells, and PMNs. See, Grundhoefer and Patterson, *Determination of Liquid-Based Cervical Cytology Specimen Adequacy Using Cellular Light Scatter and Flow Cytometry*, CYTOMETRY 46:340-344 (2001). As shown in FIGS. 4A-4I, ectocervical cells were identified in normal (WNL) and abnormal (HGSIL) cervical cell specimens by gating for a lack of CD16 and CAM 5.2 expression (CD16$^-$, CAM 5.2$^-$) (FIG. 4A, first two boxes) and ectocervical cells were analyzed for HPV E6, E7 mRNA expression using the In Cell HPV Assay of the present invention with 100 copies of HPV E6, E7 mRNA per cell used as the cut-off point for determining the percentage of cells in a sample expressing HPV E6, E7 mRNA (FIG. 4A, third box). The percentage noted at the upper right hand corner each of FIGS. 4B-4I indicates the percentage of cells in the HGSIL (FIGS. 4B-4E) and WNL (FIGS. 4F-4I) samples that express more than 100 copies of HPV mRNA per cell. In a similar vein, expression of HPV E6, E7 mRNA in endocervical cells can be analyzed by using a gating strategy that identifies CD16$^-$, CAM 5.2$^+$ expression.

Example 6

Comparative Analysis of the in Cell HPV Assay Versus the Pap Smear to Detect Abnormal SILs in a High Risk Cohort To screen for pre-malignant conditions in LBCs, LBC specimens were obtained from a high risk cohort consisting of 41 women with normal cervical cytology and 41 women with abnormal cervical cytology. As described in Example 4, abnormal cells are identified by a characteristically high nuclear to cytoplasmic ratio whereas normal squamous epithelial cells exhibit a low nuclear to cytoplasmic ratio. The women with the abnormal cells consisted of the following cytologies: 9 ASCUS, 22 LGSIL, and 10 HGSIL. For purposes of this experiment, the quantitative cut-off for a positive HPV E6, E7 mRNA result was set at 2 standard deviations from the mean of true negative. Cervical cells were stained with CD16 and CAM 5.2 (as described in Example 5) and hybridized (as described in Example 1). Ectocervical cells were differentiated from endocervical cells by both forward and orthogonal light scatter and by expression of CAM 5.2 on endocervical cells but not on ectocervical cells (Example 5, FIG. 4A). Ectocervical cells coated with neutrophils were eliminated from analysis by the presence of CD16$^+$ staining. The In Cell HPV Assay detected HPV E6, E7 mRNA in 5 of 9 ASCUS samples, 13 of 22 LGSIL samples, 10 of 10 HGSIL samples, and 3 of 41 normal (WNL) cervical cytology specimens. Two of the 3 normal samples had HPV E6, E7 mRNA confirmed by quantitative real-time RT-PCR using Taqman probes. Similar to the procedure used in Example 3, cells were considered positive for HPV E6, E7 mRNA if they exhibited an MFI greater than 200 copies per cell. For controls, HPV$^+$ HeLa cells and HPV$^-$ C33A cells were included with every run. The percentage of HPV E6, E7 mRNA expressing cells positively correlated with the cytologic diagnosis as shown in Table 1.

TABLE 1

| CYTOLOGY | % IN CELL HPV HIGH | % IN CELL HPV LOW | % IN CELL HPV MEDIAN | IN CELL HPV ASSAY PERFORMANCE |
|---|---|---|---|---|
| WNL | 5.6 | 0.1 | 0.5 | 3/41 |
| ASCUS | 7.3 | 0.1 | 1.9* | 5/9 |
| LGSIL | 12.7 | 0.1 | 2.7** | 13/22 |
| HGSIL | 46.1 | 2.1 | 13.9*** | 10/10 |

*ASCUS > WNL, p < 0.05
**LGSIL > WNL, p < 0.01; LGSIL > ASCUS,
NS (not significant)
***HGSIL > WNL, p < 0.001; HGSIL > ASCUS, p < 0.001; HGSIL > LSIL, p < 0.001

The percentage of HPV E6, E7 mRNA expressing cells in HGSILs was significantly greater than the percentage of expressing cells in WNLs (p<0.001), ASCUS (p<0.001), and LGSILs (p<0.001). Similarly, the percentage of HPV E6, E7 mRNA expressing cells in LGSILs was significantly greater than the percentage of expressing cells in WNLs (p<0.01), but not significantly greater than the percentage of HPV E6, E7 mRNA expressing cells in ASCUS, suggesting that the molecular alterations in ASCUS more closely resemble LGSIL than HGSIL. The overall sensitivity and specificity of the In Cell HPV Assay for high grade lesions was 100% and 93%, respectively.

Example 7

Comparative Analysis of the in Cell HPV Assay with the HC II HPV Test to Detect Abnormal SILs in a Low Risk Cohort To compare the ability of the In Cell HPV Assay and the HC H HPV Test to detect high grade cervical lesions, 149 LBC specimens were obtained from a low risk cohort with the following cytologies: 109 WNL, 21 ASCUS, 5 LGSIL, 12 HGSIL, and 2 with invasive cervical cancer identified by cytologic examination. Table 2 shows the results of the comparative analysis. As previously discussed, the In Cell HPV Assay tests for the presence of HPV E6, E7 mRNA while the HC II HPV Test screens for the presence of high risk HPV DNA, e.g., HPV-16 and HPV-18.

TABLE 2

| CYTOLOGY | IN CELL HPV ASSAY | HC II HPV TEST |
|---|---|---|
| WNL | 10/109 | 13/109 |
| ASCUS | 14/21 | 9/21 |
| LGSIL | 4/5 | 3/5 |
| HGSIL | 8/12 | 8/12 |
| Squamous Cell Carcinoma | 2/2 | 1/2 |
| SENSITIVITY ≥HGSIL | 71.4% | 64.2% |
| SPECIFICITY ≥HGSIL | 91% | 88% |

Similar to the results involving the high risk cohort (Example 6), the percentage of HPV E6, E7 mRNA expressing cells detected by the In Cell HPV Assay positively correlated with the cytologic diagnoses. Using HGSIL and invasive cervical cancer as an end-point, the sensitivity and specificity of In Cell HPV Assay to detect cervical abnormalities was 71.4% and 91%, respectively, and the sensitivity and specificity of the HC II HPV Test to detect cervical abnormalities was 64.2% and 88%, respectively. Both the In Cell HPV Assay and the HC II HPV Test detected 8 of 12 HGSILs, but the In Cell HPV Assay also identified an invasive cervical cancer that was missed by both real-time RT-PCR (data not shown) and the HC II HPV Test.

I claim:
1. A set of reagents consisting of:
a first pre-hybridization wash fluid;
a second pre-hybridization wash fluid;
a hybridization mix;
HPV E6, E7 mRNA specific oligonucleotides;
a first post-hybridization stringency wash;
a second post-hybridization stringency wash; and
a permeabilization reagent,
wherein said set of reagents when combined with a first and a second antibody, phosphate buffer saline, 2% fetal calf serum and a liquid-based cervical cytology specimen comprising cervical cells having 100 copies or more of HPV E6, E7 mRNA per cell, provides for determining that the cervical cells in the liquid-based cervical cytology specimen having E6, E7 mRNA copies above 100 copies of HPV E6, E7 mRNA per cell are malignant.
2. The set of reagents according to claim 1, wherein the HPV specific E6, E7 mRNA oligonucleotides are labeled.
3. The set of reagents according to claim 2, wherein the HPV specific E6, E7 mRNA oligonucleotides are labeled with fluorescein.
4. The set of reagents according to claim 3, wherein the HPV specific E6, E7 mRNA oligonucleotides are 3' and 5' labeled with fluorescein.
5. The set of reagents according to claim 1, wherein the permeablization reagent is a fixation reagent.
6. The set of reagents according to claim 1, wherein the hybridization mix consists of 5× sodium saline citrate, 30% formamide and 100 μg/mL sheared salmon sperm DNA.

* * * * *